United States Patent
Lyles

(10) Patent No.: US 7,605,141 B2
(45) Date of Patent: *Oct. 20, 2009

(54) NUCLEIC ACID ANTIOXIDANT COMPOSITIONS, METHODS FOR OBTAINING SUCH COMPOSITIONS AND FORMULATIONS THEREOF

(75) Inventor: Mark B. Lyles, Great Lakes, IL (US)

(73) Assignee: Materials Evolution and Development USA, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/539,487

(22) Filed: Oct. 6, 2006

(65) Prior Publication Data

US 2007/0112064 A1 May 17, 2007

Related U.S. Application Data

(63) Continuation of application No. 10/625,998, filed on Jul. 24, 2003, now Pat. No. 7,125,859.

(51) Int. Cl.
*A01N 43/04* (2006.01)
*A61K 31/70* (2006.01)

(52) U.S. Cl. .................. 514/44; 536/18.7; 536/22.1; 536/23.1

(58) Field of Classification Search .................. None
See application file for complete search history.

(56) References Cited

U.S. PATENT DOCUMENTS

| | | | |
|---|---|---|---|
| 4,115,597 A | 9/1978 | Pellar | 426/451 |
| 4,154,820 A | 5/1979 | Simoons | 424/175 |
| 5,064,698 A | 11/1991 | Courtright et al. | 428/35.4 |
| 5,084,293 A | 1/1992 | Todd, Jr. | 426/541 |
| 5,102,673 A | 4/1992 | Sugihara et al. | 426/124 |
| 5,214,134 A | 5/1993 | Weis et al. | 536/25.3 |
| 5,245,022 A | 9/1993 | Weis et al. | 536/24.5 |
| 5,296,249 A | 3/1994 | Todd, Jr. | 426/541 |
| 5,427,814 A | 6/1995 | Loliger et al. | 426/610 |
| 5,498,434 A | 3/1996 | Johnston | 426/541 |
| 5,545,416 A | 8/1996 | Broderick et al. | 426/3 |
| 5,567,810 A | 10/1996 | Weis et al. | 536/25.3 |
| 5,591,504 A | 1/1997 | Lieberman | 428/68 |
| 5,677,437 A | 10/1997 | Teng et al. | 536/23.1 |
| 5,919,483 A | 7/1999 | Takaichi et al. | 424/466 |
| 6,093,436 A | 7/2000 | Zhen et al. | 426/541 |
| 6,124,268 A | 9/2000 | Ghosal | 514/27 |
| 6,235,721 B1 * | 5/2001 | Ghosal | 514/25 |
| 6,333,408 B1 * | 12/2001 | Motojima et al. | 536/24.5 |
| 6,403,139 B1 | 6/2002 | Sardo et al. | 426/541 |

OTHER PUBLICATIONS

Wong et al. Biochemistry (1996), vol. 35, pp. 5756-5763.*

* cited by examiner

*Primary Examiner*—Patrick T Lewis
(74) *Attorney, Agent, or Firm*—King & Spalding L.L.P.

(57) ABSTRACT

Compositions containing purified nucleic acid wherein the nucleic acid acts as an antioxidant. Such compositions also include materials subject to oxidative damage such as antioxidants, vitamins, lipids, foods and pharmaceuticals. The invention also includes methods for preparing such compositions. These methods include dissolving the nucleic acid and a hydrophilic material in an aqueous solution, which may later be dried or further processed. Additionally, nucleic acid may be coupled with a molecule having hydrophobic and hydrophilic regions and then solubilized in a hydrophobic material. It may also be shaped into small aggregates and added to a hydrophobic material.

23 Claims, No Drawings

NUCLEIC ACID ANTIOXIDANT COMPOSITIONS, METHODS FOR OBTAINING SUCH COMPOSITIONS AND FORMULATIONS THEREOF

RELATED APPLICATION

This application is a continuation of U.S. patent application Ser. No. 10/625,998 filed Jul. 24, 2003, now U.S. Pat. No. 7,125,859 the contents of which is hereby incorporated is its entirety by reference.

FIELD OF THE INVENTION

The present invention relates to the use of a nucleic acid, such as DNA as an antioxidant. It includes nucleic acid antioxidant compositions and methods of obtaining such compositions. It also includes formulations in which a nucleic acid is used as an antioxidant.

BACKGROUND OF THE INVENTION

Antioxidants are widely used to preserve a variety of materials including food, vitamins, and pharmaceuticals. Such materials are naturally degraded by oxidants, such as oxygen radicals, present in the material or its environment. These oxidants are highly reactive and accordingly bond to and/or break down other chemicals in the material, resulting in the appearance of undesirable properties in the material. To avoid these undesirable effects, an antioxidant may be added to the material. The antioxidant has a strong affinity for oxidants and therefore provides a preferred reactant. Some such reactions may produce an undesirable by-product, but many do not. Antioxidants used for preservative purposes are selected to avoid undesirable by-products.

Foods commonly treated with antioxidants include oils, which are often used for cooking and tend to oxidize more rapidly at higher temperatures, oil-containing foods such as coffee, and dried foods. Many vitamins, including Vitamins C and E, are themselves antioxidants and therefore are rapidly degraded unless another antioxidant is provided with the vitamin. A large number of pharmaceuticals, such as synthetic estrogens, also benefit from the addition of antioxidants, especially if oxidative damage may result in a toxic by-product.

In addition to their preservative effects, many antioxidants also have physiological effects. Antioxidants are known to reduce the inflammatory response and may be used in conjunction with other drugs to treat conditions resulting from or worsened by inflammation. Additionally, it is believed that ingestion of some antioxidants, such as Vitamins C and E, helps prevent cancer and other disorders caused by oxidative damage to the body.

Accordingly, many antioxidants are available at present. These include artificial antioxidants such as butylated hydroxytoluene (BHT), butylated hydroxyanisole (BHA) and tert-butyl hydroquinone (TBHQ). Vitamin E, generally used to describe a class of chemicals known as "tocopherols", and Vitamin C, also commonly called "ascorbic acid", are also used as antioxidants. Natural antioxidants such as tea extracts and extracts of herbs such as rosemary are also used for antioxidant purposes.

SUMMARY OF THE INVENTION

The invention includes a method of preserving a material subject to oxidative damage by adding purified nucleic acid to the material. The nucleic acid reduces the rate of oxidative damage of the material.

In specific embodiments of the present invention, the nucleic acid may include DNA. The material subject to oxidative damage may be a vitamin such as Vitamin C or Vitamin E. The material subject to oxidative damage may also be a food, and antioxidant, a lipid or a pharmaceutical.

In specific embodiments where the material subject to oxidative damage is hydrophilic, the purified nucleic acid may be in an aqueous solution. Where the material subject to oxidative damage is hydrophobic, the nucleic acid may be supplied in a solvent with both hydrophilic and hydrophobic regions or as aggregates of nucleic acid less than 50 µM in diameter.

In certain embodiments, the purified nucleic acid may be sprayed on the surface of the material subject to oxidative damage.

The invention also includes a composition including a material subject to oxidative damage and an amount of purified nucleic acid sufficient to reduce the rate of oxidative damage to the material.

In specific embodiments, the nucleic acid may include DNA. The material subject to oxidative damage may be a vitamin such as Vitamin C or Vitamin E. The material subject to oxidative damage may also be a food, and antioxidant, a lipid, such as a lipid heated above ambient temperature, or a pharmaceutical, such as a synthetic estrogen.

DETAILED DESCRIPTION

For a better understanding of the invention, reference may be had to the following description of exemplary embodiments.

The present invention includes nucleic acid compositions in which the nucleic acid serves as an antioxidant. Although DNA may be best suited for most embodiments of the invention because of its durability, RNA or other nucleic acids may also be used, especially in applications where more rapid degradation of the nucleic acid is desirable. DNA and RNA may include all forms of DNA and RNA, natural and synthetic, specifically including cDNA, mRNA, rRNA and tRNA.

The nucleic acid compositions may be part of a material, such as a food, vitamin, cosmetic, or pharmaceutical. The nucleic acid compositions may also be formulated for later addition to such a material. Such compositions are biologically safe. Oxidized nucleic acid breaks down into readily degradable and non-toxic by-products. Additionally, DNA is heat-tolerant; the base pairs do not normally separate in an aqueous solution until approximately 94-96° C. and may remain bonded at higher temperatures in non-aqueous solutions. Nucleic acid antioxidants of the present invention may be provided and/or dispensed in powder liquid, gel, spray or aerosol forms, inter alia, or as a misting agent.

The nucleic acid used in the present invention may be from any source. Harvesting techniques for recovery of nucleic acid from biological sources, including techniques capable of producing commercial volumes of nucleic acids are readily known in the art. Nucleic acids may be extracted from almost any biological source. Two common sources of non-specific nucleic acid are fish sperm and calf thymus. Almost any source, animal or plant-based, yeast or bacterial may be used. These sources may be specifically developed for nucleic acid harvest or may be waste products of other commercial processes, as in the case of calf thymus. Because the present invention employs nucleic acids for their antioxidant properties alone, and not for their information coding properties, the sequences of the nucleic acid may be irrelevant.

DNA, in certain examples, may be produced by solubilization of cellular material with a detergent, followed by extraction of nucleic acid from the aqueous layer with an alcohol. Various additional steps and additives may assist in the removal of protein to obtain purer nucleic acid. Various nucleases and extraction techniques may be employed to destroy unwanted forms of nucleic acids, such as RNA. Such techniques are well known in the art.

Nucleic acids may also be synthesized artificially from nucleotides. For instance, surface catalysis techniques or oligonucleotide synthesizers may be used.

The purity of nucleic acid from biological sources used in compositions of the present invention may vary by application. In most applications, the nucleic acid will contain no more than 50% by weight residual matter from the biological source such as proteins, lipids and carbohydrates. In certain embodiments, it will contain no more than 25%, 10%, 5% or 1% by weight residual matter. Such residual matter will likely include proteins which may cause unwanted effects such as bad taste in food or spoilage. For pharmaceutical compositions, the nucleic acid may contain less than 5% by weight residual matter. Residual protein may need to be substantially removed from pharmaceutical compositions, especially injectable compositions, in order to avoid an immune response.

Nucleic acid is biodegradable and may also degrade due to oxidative damage, which is known to cause breaks in nucleic acid molecules. In many applications the rate of degradation of nucleic acid will not be significant. However, the rate may be influenced by the length of the nucleic acid molecule used and type of nucleic acid as well as by treatment of the nucleic acid.

The nucleic acid may also be crosslinked, although such crosslinking may reduce the antioxidant properties of the nucleic acid. Additionally, if the nucleic acid composition will eventually be used in a biological system, such as a human body, crosslinking agents that are toxic in such a biological system may be avoided. Crosslinking may be between chains of a single DNA molecule or between chains of two different nucleic acid molecules or in any other possible permutation. Crosslinking may be accomplished in a variety of ways, including hydrogen bonds, ionic and covalent bonds, $\pi\pi$ bonds, van der Wals forces. More specifically, crosslinking may be accomplished by UV radiation, esterification, hydrolysis, or silica compounds if biological toxicity is at issue. One specific example includes the use of siloxane bridges as described in U.S. Pat. No. 5,214,134. Intercalating agents, neoplastic agents, formaldehyde and formalin may also be used.

More than one type of crosslinking may be used in a given composition. Furthermore, crosslinking may occur between two strands of a nucleic acid molecule or between two separate nucleic acid molecules. Increased levels of crosslinking will generally slow degradation of nucleic acid, but may result in lower antioxidant activity. However, in some applications any reduced antioxidant effect may be worth the increased stability. For example, although DNA is heat-resistant, base pair-crosslinked DNA will not be as able to separate along base pairs at higher temperatures and thus will exhibit at greater degradation resistance at higher temperatures. An optimal balance between degradation and antioxidant activity for a given composition should be readily determinable to one skilled in the art.

Additionally, the nucleic acid may be methylated, ethylated, alkylated, or otherwise modified along the backbone to influence degradation rates. Generally, methylated, hemi-methylated, ethylated, or alkylated nucleic acids will degrade more slowly. Other backbone modifications affecting degradation rates include the use of heteroatomic oligonucleoside linkages as described in U.S. Pat. No. 5,677,437. Such backbone modifications may also affect the solubility of nucleic acid, for instance rendering it more lipid soluble. Backbone modifications may also increase the antioxidant capacity of nucleic acid.

Nucleic acids may also be capped to prevent degradation, influence solubility, or influence antioxidant effects. Such caps are generally located at or near the termini of the nucleic acid chains. Examples of capping procedures are included in U.S. Pat. Nos. 5,245,022 and 5,567,810.

The size of the nucleic acid molecules used in compositions of the present invention may vary from as small as 2 bases to as long as 10,000 bases or more. In general, most compositions will contain nucleic acid molecules with a variety of lengths. In exemplary embodiments, the average nucleic acid molecule length may be between 50 and 500 bases. However, smaller nucleic acid molecules may be used in certain embodiments, particularly those where the nucleic acid is used as an antioxidant for an oil or other lipid-rich material in which it is not readily soluble. Alternatively, larger nucleic acid molecules may be used in such materials to form small nucleic acid particles which may be dispersed throughout the material.

The compositions of the present invention may include nucleic acid as the sole antioxidant, or they may also include other antioxidants, including both natural and synthetic antioxidants.

The following examples are provided only to illustrate certain aspects of the invention and are not intended to embody the total scope of the invention or the totality of any aspect thereof. Variations of the exemplary embodiments of the invention below will be apparent to one skilled in the art and are intended to be included within the scope of the invention.

EXAMPLES

Example 1

Nucleic Acid Stabilized Vitamin Compositions

Although Vitamin C is commonly sold as a nutrient supplement, because it is a potent antioxidant it has a very limited shelf-life. Furthermore, Vitamin C becomes a mild pro-oxidant after an oxidative reaction. Therefore, Vitamin C supplements that have been substantially oxidized may actually be harmful. Nucleic acid may be added to a solution of Vitamin C in an alcohol. The solution may be dried to produce Vitamin C powder or tablets. The optimal proportion of nucleic acid to Vitamin C may be determined by mixing various proportions in alcohol solutions, drying the solutions, and storing the dried powders for approximately 6 months (the normal shelf-life of Vitamin C). Vitamin C levels or antioxidant activity may then be measured, for instance by measuring reactivity with diphenyl picryl hydrazine. In certain embodiments, the optimal proportion of nucleic acid to Vitamin C by weight will fall between 60% and 80%. Examples of antioxidant formulations and methods for testing these formulations are provided in U.S. Pat. No. 6,235,721 of Ghosal (the "'721 Patent"). Although the '721 Patent addresses stabilization of Vitamin C and other compounds using a fruit extract, the methodologies should be applicable to nucleic acid as well.

Nucleic acid may also be used as an antioxidant for Vitamin E. Methods such as those described in Example 5 may be used to increase solubility of nucleic acid in Vitamin E. Alternatively, the nucleic acid may be allowed to from small aggregates in a mixture with the Vitamin E, or the Vitamin E may be allowed to form small aggregates in a mixture with the nucleic acid. Proportions of nucleic acid used in Vitamin E formulations may be similar to those used in Vitamin C formulations, although more nucleic acid by weight may be recommended.

Nucleic acid may similarly be added to other vitamin compositions, which may or may not contain Vitamins C or E. In particular, Vitamin A supplements may be prepared using methodologies similar to those used for Vitamin E.

Example 2

Nucleic Acid Stabilized Lotion Compositions

Lotions, creams and other similar preparations, whether used for cosmetic, topical pharmaceutical, or other purposes, are often formed by mixing component lipids and other chemicals at approximately 80-85° C. Lipids may oxidize during this heating process, so the addition of an antioxidant capable of enduring heating is desirable. Nucleic acid may be added to such a mixture prior to or during heating to help prevent oxidation of lipid or other lotion components. The amount of nucleic acid in such lotions may be varied depending upon the oxidative reactivity of the lotion components. For many lotions, between 0.1 and 5% nucleic acid by weight may be sufficient. Appropriate nucleic acid proportions may be tested by allowing samples to sit for acceptable shelf-life time intervals, for example one year, and then measuring the amount of oxidative damage to one or more indicator compounds.

The above method may also be used to prepare lotions containing antioxidants, such as Vitamins C and E, or topical ointments which will contain pharmaceuticals susceptible to oxidative damage.

Lotion, cream and topical antioxidant formulations may further be prepared as described in U.S. Pat. No. 6,124,268 (the "'268 Patent"). Although the '268 patent relates to the use of a fruit extract as an antioxidant, its methodologies should be applicable to nucleic acids as well. Methods for increasing solubility of nucleic acids in hydrophobic substances are described in Example 5. Alternatively, nucleic acids may be allowed to form small aggregates within the lotion.

Example 3

Nucleic Acid Stabilized Synthetic Estrogens

Synthetic estrogens are used for a variety of medical reasons, ranging from birth control to treatment of hormone deficiencies. However, synthetic estrogens tend to be unstable, especially in damp environments. One source of instability, hydrolysis of the synthetic molecules, may be combated using a buffer. However, use of the buffer only produces a shelf-life of around 6 months. Addition of 0.25 to 6 moles of an antioxidant has been shown to increase shelf-life up to two years without significant degradation of alkali metal synthetic estrogen sulfates. (See U.S. Pat. No. 4,154,820 of Simoons, the "'820 Patent".) Nucleic acid may be used in as an antioxidant in synthetic estrogen compositions and tested for efficiency as described in the '820 Patent. Because both nucleic acid and most synthetic estrogens may be solubilized in water, aqueous solutions may be easily prepared and used or further processed to gelcap or dry formulations.

Example 4

Nucleic Acid Stabilized Gum Base and High-Temperature Oils

Like lotions, gum base must often be heated during preparation. This allows significant oxidation of fats and oils in the gum base. Although gum base processing temperatures are often higher than the denaturation temperature of DNA, they are not so high as to cause breakdown of the nucleic acid backbone. Many of DNA's antioxidant properties do not depend upon a helical structure, therefore DNA should continue to function as an antioxidant even in denatured form. Additionally, the DNA molecule may be modified by crosslinking to prevent denaturation at higher temperatures.

Addition of between 7-2000 parts per million of antioxidant has been shown to significantly reduce oxidative damage to gum base, particularly during heat processing steps. (See U.S. Pat. No. 5,545,416 to Broderick et al., the "'416 Patent".) Although the '416 Patent uses a synthetic antioxidant, its techniques should be applicable to the preparation of a gum base with nucleic acid antioxidant. Additionally, as described in the '416 Patent, larger amounts of nucleic acid may be added in initial processing stages to ensure that sufficient amounts remain after heat processing. This technique of adding larger amounts of nucleic acid prior to heat processing may also be used the processing of other materials.

This methodology may also be useful for the addition of nucleic acid as an antioxidant to oils used for frying, which may also involve the use of temperatures above the denaturation point of DNA. Another methodology for maintaining a constant nucleic acid concentration in cooking oils that may be used with nucleic acid as an antioxidant is described in U.S. Pat. No. 4,115,597 of Pellar.

Example 5

Solubilization of Nucleic Acid in Lipids

Nucleic acid is relatively insoluble in hydrophobic compositions, such as fats, Vitamin E and other lipids. In order to increase its solubility, it may be added to the hydrophobic composition in a manner similar to that described in U.S. Pat. No. 5,084,293 of Todd, Jr. (the "'293 Patent") for ascorbic acid. Generally, the process in the '293 Patent involves forming an anhydrous paste of the nucleic acid in a substance that has both hydrophobic and hydrophilic properties.

Example 6

Nucleic Acid Aggregates

Nucleic acid may also be added to lipids by the incorporation of small nucleic acid aggregates into the lipids. These aggregates are preferably less than 50 microns in size. U.S. Pat. No. 5,296,249 of Todd, Jr. (the "'249 Patent") discloses a method of producing and using Vitamin C microparticles of approximately less than 38 microns. The '249 Patent shows that antioxidants do not have to be solubilized in a lipid to reduce oxidative damage. Small particles dispersed in the lipid are also functional for this purpose. The wet milling techniques of the '249 Patent may be used for nucleic acid in solution in which it is insoluble or only slightly soluble, such as a solution with high alcohol content. Alternatively, small nucleic acid particles may be produced by dropping aqueous nucleic acid solution into a condensing solution, such as a high alcohol content solution. Other methods of producing very small particles of nucleic acid are also possible. The size and type of the nucleic acid molecule may affect the size of the aggregate formed. Micro or nanoparticles of nucleic acid may be preferred for many uses.

Example 7

Treatment of Fruits and Vegetables

Harvested fruits and vegetables deteriorate rapidly for a variety of reasons, one of which is the oxidation of molecules in their surface layers. In order to prevent this oxidation, U.S. Pat. No. 6,403,139 to Sardo et al. (the "'139 Patent") discloses a method for applying antioxidants to harvested fruits and vegetables. Similar application techniques may be used to apply nucleic acid as an antioxidant. The nucleic acid may be applied at a lower temperature than in the '139 Patent if it is in an aqueous solution. Alternatively, if the nucleic acid is first mixed in a hydrophobic compound as described in Examples 5 and 6, if the hydrophobic compound is solid at room temperature it may remain on the fruit or vegetable more readily than nucleic acid alone, but will likely benefit from elevated application temperatures as described in the '139 Patent.

Example 8

Nucleic Acid and Additional Antioxidant Compositions

U.S. Pat. No. 5,498,434 (the "'434 Patent") and U.S. Pat. No. 5,427,814 (the "'814 Patent") describe beneficial effects of providing more than one antioxidant in a given formulation. Specifically, both observe a beneficial effect when Vitamin E and lecithin are used together with either Vitamin C or oil of rosemary. Nucleic acid may also be used in such a mixture, with expected beneficial effects. Such formulation may be prepared as described in the '814 and '434 Patents. Because nucleic acid is hydrophilic, the process described in the '814 Patent may be preferred, with nucleic acid used in a manner similar to or in place of Vitamin C.

Example 9

Coupled Antioxidant Systems

U.S. Pat. No. 6,093,436 describes an antioxidant system in which an enzyme, glucose oxidase, serves as the primary antioxidant and an inorganic oxygen scavenger serves as a repository. The system is tailored for a beverage system. Nucleic acid may be in place of an inorganic oxygen scavenger in systems such as these.

Example 10

Nucleic Acid Effervescent Antioxidant

U.S. Pat. No. 5,919,483 of Takaichi et al. (the "'483 Patent") describes an effervescent composition containing an antioxidant. The composition is water soluble and may be used to store antioxidant then allows its ready use in an aqueous solution. Compositions similar to those described in the '483 Patent may be prepared using nucleic acid as the antioxidant.

Example 11

Nucleic Acid Antioxidant for Rapid Degradation

In certain applications long-lasting antioxidants are not required or desirable. For example, short-lived antioxidants may be useful in neutralizing the effects of chemical weapons such as mustard gas. When such short-lived antioxidants are desirable then RNA or shorter nucleic acid molecules may be used.

Example 12

Other Antioxidant Uses

Nucleic acid antioxidants of the present invention may be used to neutralize any oxide, including peroxides, carbonyl radicals, carboxy radicals and ozones. They may also be used to mitigate effects of biological materials that directly or indirectly produce oxides such as prostaglandins and interleukins or other inflammatory mediators or by-products. Finally, oxidative products of any source such as UV radiation, mustard gas and alkylating agents may be neutralized or their effects mitigated using antioxidants of the present invention. For example, nucleic acid antioxidants may mitigate effects of blistering agents by neutralizing oxidative products and reducing inflammation.

All of the compositions and/or methods disclosed and claimed herein can be made and executed without undue experimentation in light of the present disclosure. While the compositions and methods of this invention have been described in terms of specific embodiments, it will be apparent to those of skill in the art that variations may be applied to the compositions and/or methods and in the steps or in the sequence of steps of the methods described herein without departing from the concept, spirit and scope of the invention. All such similar substitutes and modifications apparent to those skilled in the art are deemed to be within the spirit, scope and concept of the invention.

What is claimed is:

1. A method of preserving a hydrophilic material subject to oxidative damage comprising adding purified DNA between 50 and 500 bases in length to an aqueous solution of the hydrophilic material, wherein the DNA reduces the rate of oxidative damage of the hydrophilic material.

2. The method of claim 1, wherein the material subject to oxidative damage is Vitamin C.

3. A method of preserving a hydrophobic material subject to oxidative damage comprising adding purified DNA between 50 and 500 bases in length in a solvent with both hydrophilic and hydrophobic regions to the hydrophobic material, wherein the DNA reduces the rate of oxidative damage of the hydrophobic material.

4. The method of claim 1, wherein the material subject to oxidative damage is a vitamin.

5. The method of claim 1, wherein the material subject to oxidative damage is a food.

6. The method of claim 1, wherein the material subject to oxidative damage is an antioxidant.

7. The method of claim 3, wherein the material subject to oxidative damage is a lipid.

8. The method of claim 1, wherein the material subject to oxidative damage is a pharmaceutical.

9. The method of claim 1, further comprising spraying the purified nucleic acid onto the surface of the material subject to oxidative damage.

10. The method of claim 3, wherein the material subject to oxidative damage is Vitamin E.

11. The method of claim 3, wherein the material subject to oxidative damage is a vitamin.

12. The method of claim 3, wherein the material subject to oxidative damage is a food.

13. The method of claim 3, wherein the material subject to oxidative damage is an antioxidant.

14. The method of claim 3, wherein the material subject to oxidative damage is a pharmaceutical.

15. The method of claim 3, further comprising spraying the purified nucleic acid onto the surface of the material subject to oxidative damage.

16. A method of preserving a hydrophobic material subject to oxidative damage comprising adding aggregates of purified nucleic acid between 50 and 500 bases in length and less than 50 μM in diameter to the hydrophobic material, wherein the nucleic acid reduces the rate of oxidative damage of the hydrophobic material.

17. The method of claim 16, wherein the material subject to oxidative damage is Vitamin E.

18. The method of claim 16, wherein the material subject to oxidative damage is a vitamin.

19. The method of claim 16, wherein the material subject to oxidative damage is a food.

20. The method of claim 16, wherein the material subject to oxidative damage is an antioxidant.

21. The method of claim 16, wherein the material subject to oxidative damage is a lipid.

22. The method of claim 16, wherein the material subject to oxidative damage is a pharmaceutical.

23. The method of claim 16, further comprising spraying the purified nucleic acid onto the surface of the material subject to oxidative damage.

\* \* \* \* \*